United States Patent
Liebeneiner (10) Patent No.: US 9,957,201 B2
(45) Date of Patent: May 1, 2018

(54) PRODUCING LIQUID FERTILIZER IN A BIOGAS PLANT

(71) Applicant: BEKON GmbH, Marienfeld (DE)

(72) Inventor: Rolf Liebeneiner, Stockdorf (DE)

(73) Assignee: BEKON GmbH, Marienfeld (DE)

( * ) Notice: Subject to any disclaimer, the term of this patent is extended or adjusted under 35 U.S.C. 154(b) by 260 days.

(21) Appl. No.: 14/980,905

(22) Filed: Dec. 28, 2015

(65) Prior Publication Data
US 2016/0107946 A1 Apr. 21, 2016

Related U.S. Application Data

(63) Continuation-in-part of application No. PCT/EP2014/064338, filed on Jul. 4, 2014.

(30) Foreign Application Priority Data

Jul. 5, 2013 (DE) ...................... 10 2013 211 3258

(51) Int. Cl.
*C12P 5/02* (2006.01)
*C05F 17/00* (2006.01)
(Continued)

(52) U.S. Cl.
CPC ........ *C05F 17/009* (2013.01); *C05F 17/0258* (2013.01); *C05G 3/0064* (2013.01);
(Continued)

(58) Field of Classification Search
None
See application file for complete search history.

(56) References Cited

U.S. PATENT DOCUMENTS 3,745,113 A * 7/1973 Fuchs ...................... C02F 3/12
210/219
3,864,247 A * 2/1975 Fuchs ...................... C02F 3/12
210/608
(Continued)

FOREIGN PATENT DOCUMENTS

CN 201670835 U 6/2010
DE 102007037187 8/2007
(Continued)

OTHER PUBLICATIONS

Office action dated Mar. 19, 2014 from the German Patent Office in the related foreign application DE102013213258.1 citing the references above (7 pages).
(Continued)

*Primary Examiner* — Wayne Langel
(74) *Attorney, Agent, or Firm* — Imperium Patent Works; Darien K. Wallace (57) ABSTRACT

A biogas plant produces both methane and liquid fertilizer by fermenting biomass. The plant includes a fermenter, a percolate tank and a sanitation tank located inside the percolate tank. Dry fermentation takes place in the fermenter and generates methane and a percolate. The percolate is circulated between the fermenter and the percolate tank. Percolate that is returned from the percolate tank to the fermenter is sprinkled over the biomass. A portion of the percolate is transferred from the percolate tank into the sanitation tank. The percolate in the sanitation tank is sanitized by heating to a Celsius temperature between 45° and 65° for a period of at least five days. The percolate in the sanitation tank is heated using both a heating device in the sanitation tank as well as heat generated from a thermophilic fermentation reaction occurring in the percolate tank. The sanitized percolate is used as liquid fertilizer.

13 Claims, 4 Drawing Sheets

(51) Int. Cl.
C12M 1/107 (2006.01)
C12M 1/00 (2006.01)
C12M 1/34 (2006.01)
C12M 1/02 (2006.01)
C12M 1/36 (2006.01)
C05F 17/02 (2006.01)
C05G 3/00 (2006.01)
C12M 1/26 (2006.01)
C12M 1/12 (2006.01)

(52) U.S. Cl.
CPC .......... C12M 21/04 (2013.01); C12M 23/40 (2013.01); C12M 23/58 (2013.01); C12M 29/00 (2013.01); C12M 29/02 (2013.01); C12M 29/18 (2013.01); C12M 29/26 (2013.01); C12M 33/00 (2013.01); C12M 33/14 (2013.01); C12M 37/02 (2013.01); C12M 41/14 (2013.01); C12M 41/16 (2013.01); C12M 41/22 (2013.01); C12M 41/24 (2013.01); C12M 41/48 (2013.01); C12M 47/16 (2013.01); C12P 5/023 (2013.01); Y02E 50/343 (2013.01); Y02P 20/145 (2015.11); Y02W 30/43 (2015.05); Y02W 30/47 (2015.05)

(56) References Cited

U.S. PATENT DOCUMENTS

| | | | |
|---|---|---|---|
| 4,139,640 A * | 2/1979 | Kipp, Jr. | C05F 3/00 426/55 |
| 4,758,344 A | 7/1988 | Wildenauer | 210/603 |
| 5,538,860 A * | 7/1996 | Castelli | C05F 17/00 220/908 |
| 6,200,475 B1 * | 3/2001 | Chen | B09B 3/00 210/613 |
| 2009/0107913 A1 | 4/2009 | Johnson | 210/604 |
| 2010/0159571 A1 | 6/2010 | Lutz | 435/286.5 |
| 2010/0212384 A1 * | 8/2010 | Nakasaki | A01G 1/044 71/5 |
| 2011/0236947 A1 * | 9/2011 | Lutz | C10L 3/08 435/167 |
| 2012/0115185 A1 * | 5/2012 | Eggersmann | C12M 21/04 435/41 |
| 2012/0122175 A1 * | 5/2012 | Eggersmann | C12M 21/04 435/167 |
| 2012/0171742 A1 | 7/2012 | Roelofs | 435/167 |
| 2012/0312742 A1 | 12/2012 | Sassow | 210/603 |
| 2013/0055635 A1 * | 3/2013 | Harman | A01G 31/001 47/58.1 R |
| 2013/0065290 A1 * | 3/2013 | Mate | C02F 11/04 435/167 |
| 2015/0068259 A1 * | 3/2015 | Lutz | C12M 21/04 71/8 |
| 2015/0203874 A1 * | 7/2015 | Bonhomme | C12M 21/04 435/167 |

FOREIGN PATENT DOCUMENTS

| | | |
|---|---|---|
| EP | 0346282 B1 | 5/1989 |
| EP | 0429883 A2 | 11/1990 |
| EP | 1301583 B1 | 7/2001 |
| EP | 1717306 A1 | 4/2006 |
| EP | 2275526 A2 | 9/2009 |
| EP | 2202292 A1 | 12/2009 |
| EP | 2420328 A1 | 8/2011 |
| FR | 2981086 A1 | 10/2011 |
| GB | 2407088 A | 10/2003 |
| WO | WO 2012/115589 A1 | 2/2012 |

OTHER PUBLICATIONS

English translation of the Mar. 19, 2014 Office action from the German Patent Office in DE102013213258.1 listed in R above. (5 pages).

Qing, Peng, et al. "Correlation Characteristics between Anaerobic Digestion and Aerobic Post-treatment for Treating Wastewater on Livestock Farm [J]." China Biogas 4 (2010): 002.

Office action dated Aug. 17, 2016 from the Chinese Patent Office in the related foreign application CN201480035584.4 citing the references above (6 pages).

English translation of the Aug. 17, 2016 Office action from the Chinese Patent Office in CN201480035584.4 listed in D above. (10 pages).

* cited by examiner

PRODUCING LIQUID FERTILIZER IN A BIOGAS PLANT

CROSS REFERENCE TO RELATED APPLICATION

This application is filed under 35 U.S.C. § 111(a) and is based on and hereby claims priority under 35 U.S.C. § 120 and § 365(c) from International Application No. PCT/EP2014/064338, filed on Jul. 4, 2014, and published as WO 2015/001091 A1 on Jan. 8, 2015, which in turn claims priority from German Application No. 1020132113258.1, filed in Germany on Jul. 5, 2013. This application is a continuation-in-part of International Application No. PCT/EP2014/064338, which is a continuation of German Application No. 1020132113258.1. International Application No. PCT/EP2014/064338 is pending as of the filing date of this application, and the United States is an elected state in International Application No. PCT/EP2014/064338. This application claims the benefit under 35 U.S.C. § 119 from German Application No. 1020132113258.1. The disclosure of each of the foregoing documents is incorporated herein by reference.

TECHNICAL FIELD

The present invention relates to a method of producing a liquid fertilizer and a biogas plant for the realization of the method.

BACKGROUND

Biogas plants serve to produce biogas by way of fermentation of biomass in so-called fermenters. Depending on the type of the biomass to be fermented, fermentation can be dry fermentation or wet fermentation. The biogas contains mainly methane. As is known from European patent EP1301583 B1, during dry fermentation, the biomass that is used is dry and contains interfering substances, such as sand, rocks, and woody or fibrous components. The biomass includes biodegradable waste (organic waste of animal or plant origin that can be decomposed by micro-organisms and/or enzymes), dung (a mixture of manure and litter) or grass. The biomass ingredients can cause problems in wet-fermentation biogas plants. In particular, the biomass used for dry fermentation can be stacked, but not pumped. Although referred to as "dry" fermentation, the "dry" is only relative to wet fermentation. The biomass (also called the substrate) in dry fermentation can have a water content of up to 70%. In most cases, the biomass is moistened with a liquid before and/or during fermentation in order to start and/or maintain the necessary microbial processes, i.e., the anaerobic decomposition that takes place in the fermenters. Water enriched with suitable bacterial cultures can also be used as the liquid. Often part of the seepage (also called the percolate) is used as the liquid. The percolate is removed from a bottom section of the fermenter and is again sprinkled over the biomass.

However, by far the largest part of the percolate produced during fermentation is collected in tanks in order to be applied to agricultural fields for fertilization. Section 2.2.3 of the German Biodegradable Waste Ordinance (BioAbfV) of Apr. 4, 2013 defines mandatory "sanitation" procedures for handling percolate that is applied to agricultural fields. In particular, the percolate must be heated to a temperature of 70° C. for an hour in order to achieve the defined sanitary quality and environmental compatibility based on pathogen content, weed seeds and other undesirable components such as salmonella, clubroot and tomato seeds.

Biogas plants with solid fermenters and percolate circulation are known from GB 2407088 A as well as from EP 2275526 A2. The fermentation process in the percolate tank can be thermophilic so that the percolate is sanitized in the tank. However, because the percolate tank is part of the percolate circuit, the sanitized percolate is returned to the fermenter and is contaminated again. A permanent sanitation of the percolate can only be achieved when no more percolate is added from the fermenter or returned to the fermenter.

A method of producing liquid fertilizer from percolate is sought that does not result in recontamination of the sanitized percolate as occurs in GB 2407088 A and EP 2275526 A2. A method is sought in which percolate can be drained from the biogas plant during operation of the fermenter. Furthermore, it is an object of the invention to provide a biogas plant for implementing the method.

SUMMARY

The invention relates to a method of producing a liquid fertilizing agent and a biogas plant for performing the method. Percolate must be sanitized in order for the percolate to be applied to fields as liquid fertilizer. Conventional biogas plants have both a solids digester and a percolate circuit. However, the novel biogas plant sanitizes the percolate separately from the percolate circuit using heat generated by thermophilic bacterial processes acting on the percolate in the percolate circuit. The percolate tank is part of the percolate circuit, so sanitized percolate would be recontaminated if fed back into the digester. By providing a percolate tank and a separate sanitizing tank that are different components, the sanitizing can be performed independently of and in parallel with the percolate circuit in which percolate circulates between the digester and the percolate tank. Whenever excess percolate accumulates in the percolate circuit, the excess percolate is transferred to the sanitizing tank and sanitized there while separate from the percolate in the percolate circuit. Thus, surplus percolate that accumulates can be sanitized even while biogas is being produced in the digester. In addition, separating the percolate tank from the sanitizing tank prevents percolate that has already been sanitized from becoming recontaminated. Therefore, the sanitizing need be performed only once.

A biogas plant produces both methane and liquid fertilizer by fermenting biomass. The liquid fertilizer has a sanitary quality that is acceptable for spraying on fields used to grow produce for human consumption. The plant includes a fermenter, a percolate tank and a sanitation tank. The sanitation tank is located inside the percolate tank in an elevated position coaxially to the percolate tank such that an upper end of the sanitation tank is level with a top end of the percolate tank. Dry fermentation takes place in the fermenter and generates methane and a percolate. The percolate is circulated through a percolate pipe between the fermenter and the percolate tank. Percolate that is returned from the percolate tank to the fermenter is sprinkled over the biomass. A portion of the percolate is transferred from the percolate tank into the sanitation tank. The percolate in the sanitation tank is heated to a Celsius temperature between 45° and 65° for a period of at least five days and is thereby sanitized. The percolate in the sanitation tank is heated using both a heating device in the sanitation tank as well as heat generated from a thermophilic fermentation reaction occurring in the percolate tank. The biogas plant includes a temperature adjustment device coupled to the heating device. The temperature adjustment device is used to maintain the percolate in the sanitation tank between 45° and 65° Celsius. The sanitized percolate is used as the liquid fertilizer A method of producing methane and liquid fertilizer in a biogas plant sanitizes the fertilizer using heat generated from thermophilic fermentation of percolate produced by fermenting biomass. The methane is generated by fermenting the biomass in a fermenter in which the percolate is a byproduct. The percolate is transferred from the fermenter to a percolate tank. The percolate is returned from the percolate tank to the fermenter and sprinkled over the biomass to promote a dry fermentation reaction. A first portion of the percolate is transferred from the percolate tank into a sanitation tank that is arranged concentrically inside the percolate tank. The percolate contained in the sanitation tank is sanitized by heating to a Celsius temperature between 45° and 65° for a period of at least five days.

The first portion of the percolate passes through a valve from the percolate tank into the sanitation tank. The valve is closed during the period of at least five days while the percolate contained in the sanitation tank is heated to the Celsius temperature between 45° and 65°. This prevents the percolate in the sanitation tank from being recontaminated by unsanitized percolate from the percolate tank. The heating of the percolate contained in the sanitation tank is performed using heat generated from a thermophilic fermentation reaction of the percolate in the percolate tank as well as by using a heating device located inside the sanitation tank. The percolate is then drained from the sanitation tank and used as the liquid fertilizer. A second portion of the percolate is transferred from the percolate tank into the sanitation tank after the draining of the first portion of percolate from the sanitation tank.

Other embodiments and advantages are described in the detailed description below. This summary does not purport to define the invention. The invention is defined by the claims.

BRIEF DESCRIPTION OF THE DRAWINGS

The accompanying drawings, where like numerals indicate like components, illustrate embodiments of the invention.

DETAILED DESCRIPTION

Reference will now be made in detail to some embodiments of the invention, examples of which are illustrated in the accompanying drawings.

Figure 1:
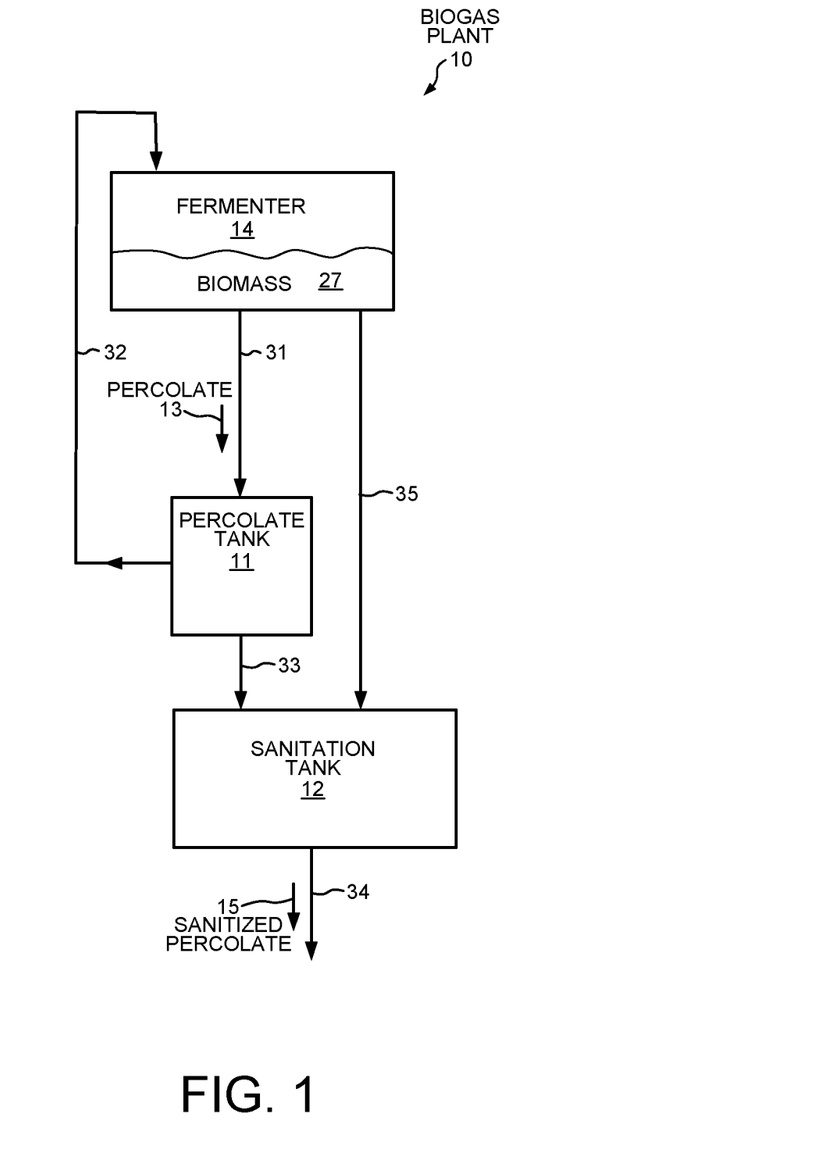
FIG. 1 is a schematic illustration of principles used in a first embodiment of the invention.

FIG. 1 shows a biogas plant 10 in which a percolate tank 11 and the sanitation tank 12 are different components, which allows the sanitation function of the biogas plant to be carried out independently and in parallel with the circulation of percolate 13 between the fermenter 14 and the percolate tank 11. Separating the percolate tank 11 and the sanitation tank 12 allows excess percolate 13, whenever produced, to be transferred to the sanitation tank 12 and sanitized there separately from the percolate in the percolate circuit between the fermenter 14 and the percolate tank 11. As a result, excess percolate 13 produced during biogas generation in the fermenter 14 can be sanitized. The separation of percolate tank 11 and sanitation tank 12 also prevents a recontamination of the percolate that was already sanitized. Thus, sanitation need be carried out only once.

The decontaminated percolate 15 from the sanitation tank 12 can be stored temporarily in a storage tank 16. The transfer of contaminated percolate 13 from the percolate tank 11 to the sanitation tank 12 is demand-based, i.e., either excess percolate 13 must be drained from the percolate tank 11, or there is a demand to use the percolate as liquid fertilizer. The contaminated percolate 13 is drained into the sanitation tank 12 based on the fill level in the percolate tank 11 and/or in the sanitation tank 12. The transfer of contaminated percolate 13 from the percolate tank 11 into the sanitation tank 12 is realized depending on the fill level of the percolate in the sanitation tank 12 and/or the fill level of the contaminated percolate 13 in the percolate tank 11 and/or the fill level of the sanitized percolate 15 in the storage tank 16. The transfer of contaminated percolate 13 from the percolate tank 11 into the sanitation tank 12 is always realized only after complete drainage of the sanitized percolate 15 from the sanitation tank 12.

Figure 2:
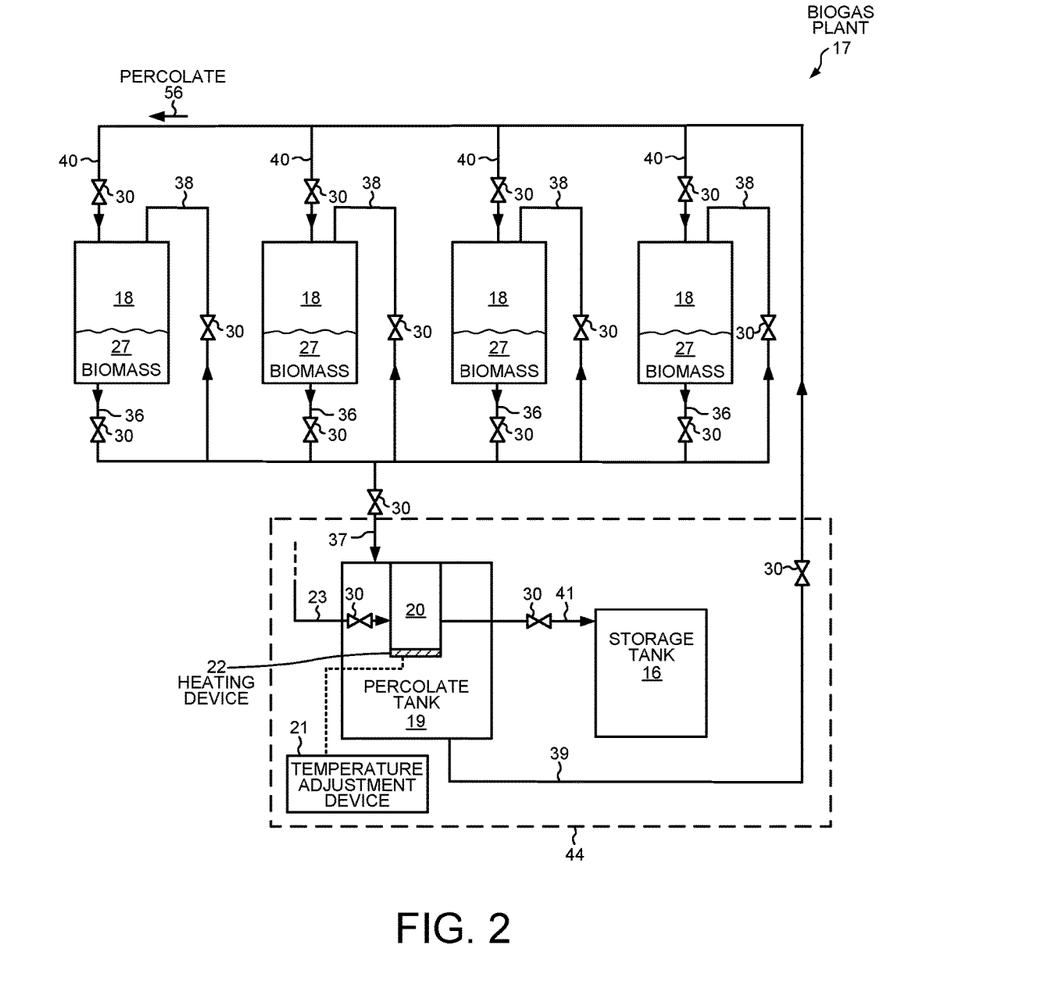
FIG. 2 is a biogas plant according to a second embodiment of the invention.

FIG. 2 illustrates a biogas plant 17 with multiple fermenters 18, each of which operates in batch mode to generate methane. The biogas plant 17 includes a percolate tank 19, a sanitation tank 20, and a temperature adjustment device 21, which includes a heating device 22. The percolate tank 19 is connected to each fermenter 18 to form a percolate circuit. The sanitation tank 20 for the storage of percolate 15 is connected to the percolate tank 19. The percolate tank 19 and the sanitation tank 20 are separate and different components, although in the embodiment of FIG. 2, the sanitation tank 20 is located inside the percolate tank 19.

The temperature adjustment device 21 maintains the Celsius temperature T inside the sanitation tank 20 in the range of 65°>T>45°, preferably 60°>T>50°. This temperature range allows for the thermophilic temperature treatment of the percolate contained in the sanitation tank 20. As there are different types of "thermophilic" fermentation reactions, those reactions that take place in the Celsius temperature range of 65°>T>45°, preferably 60°>T>50°, take place inside the sanitation tank 20. Although the disclosed sanitation temperature range is lower than that specified by the German Biodegradable Waste Ordinance (BioAbfV), the same sanitation result can be achieved if the duration of the thermophilic fermentation sanitation step is extended. The energy and heating costs of the sanitation step are thereby reduced. An acceptable sanitary quality for producing liquid fertilizer for use on fields growing produce for human consumption can be achieved by heating the percolate in the sanitation tank 20 to above 45° Celsius for at least five days. This sanitary quality has killed undesirable components such as salmonella bacteria, clubroot, tomato seeds and weed seeds.

The sanitation tank 20 is arranged inside the percolate tank 19. This arrangement is possible in most cases because the sanitation tank 20 is normally smaller than the percolate tank 19, and it is advantageous for structural reasons because only a single foundation is required. Furthermore, no or only short connecting pipes are necessary between the two tanks. Finally, the energy required to maintain the temperature of the percolate 13 in the sanitation tank 20 is reduced in comparison to locating the sanitation tank 20 outside the percolate tank 19. Energy can be saved even if the sanitation tank 20 is located only partially inside the percolate tank 19.

However, the sanitation tank 20 is preferably completely integrated into the percolate tank 19 for thermal reasons so that the sanitation tank 20 is completely surrounded by contaminated percolate 13.

In one embodiment, the percolate tank 19 and the sanitation tank 20 are coaxially oriented and have a common vertical axis. Thus, the tanks 19-20 are arranged concentrically to each other. Although, the sanitation tank 20 can be located anywhere inside the percolate tank 19, a concentric arrangement is preferred for structural reasons. The tanks 19-20 can be less expensively manufactured if they are shaped as straight cylinders with circular bases. Alternatively, the tanks can be elongated and rectangular with square bases. The shape of the percolate tank 19 need not be identical to the shape of the sanitation tank 20.

The sanitation tank 20 is directly connected to a fermenter 18 for the intake of percolate 13 through a percolate pipe 23. Thus, the sanitation tank 20 is connected to the fermenter 18 directly via the percolate pipe 23 and indirectly via the percolate tank 19. As a result, an interim storage of percolate in the percolate tank is not necessary. The connection between the sanitation tank 20 and the fermenter 18 is opened and closed on a demand basis or situation basis.

A manually adjustable valve or an electromagnetic valve (or several valves) is used for demand-based activation. The automatic filling of the sanitation tank 20 directly from the fermenter 18 is preferably performed depending on the fill level of the percolate in the sanitation tank 20 or in the percolate tank 19. For example, from a technical standpoint it is easier with a fully filled percolate tank 19 not to begin by draining percolate from the percolate tank 19 into the sanitation tank 20 and then to refill the percolate tank 19 with percolate 13 from the fermenter 18.

The temperature adjustment device 21 includes the heating device 22. Depending on the arrangement of the sanitation tank 20 and the percolate tank 19 (next to each other or one inside the other), the heating device 22 for temperature control of the percolate 15 is designed in different ways. The heating device 22 is designed so that it extends into at least a part of the bottom and/or at least a part of the wall of the sanitation tank 20 in order to achieve and maintain the desired temperature in a way that is as consistent as possible. Alternatively, heating elements can be arranged inside the sanitation tank 20, preferably directly in contact with the percolate 15. With a concentric inter-arrangement of the sanitation tank 20 inside the percolate tank 19, heating elements inside the sanitation tank 20 in combination with the heating through the percolate 13 in the percolate tank can ensure a consistent heating of the sanitized percolate 15 in the sanitation tank. In such a case, the heating power can be reduced. The temperature adjustment device 21 also includes a cooling device that can, for example in the summer, prevent the overheating of the percolate 15 in the sanitation tank 20.

In addition, the temperature adjustment device 21 includes a heat exchanger for heat transfer between the percolate tank 19 and the sanitation tank 20 and/or between the fermenter 18 and the sanitation tank 20. Depending on the marginal conditions (climatic conditions, size and design of the tanks, etc.), the heat transmitted from the percolate tank 19 via the heat exchanger to the sanitation tank 20 can be sufficient to achieve and maintain the thermophilic temperature, or heat from the above-mentioned heating device must be added. In case of the above-mentioned arrangement of the sanitation tank 20 inside the percolate tank 19, in particular when the sanitation tank 20 is encompassed by percolate 13, at least part of the wall of the sanitation tank 20 functions as an indirect heat transmitter. In case of metal tanks, naturally the entire wall acts as a heat exchanger.

The temperature of the interior of the fermenter 18 can be controlled using heating devices in the bottom or the wall for better control of the fermentation process. A particularly uniform and efficient temperature control of the interior of the fermenter 18 can be achieved using a heating device in the style of a floor heating in the bottom and/or in at least one wall.

Figure 3:
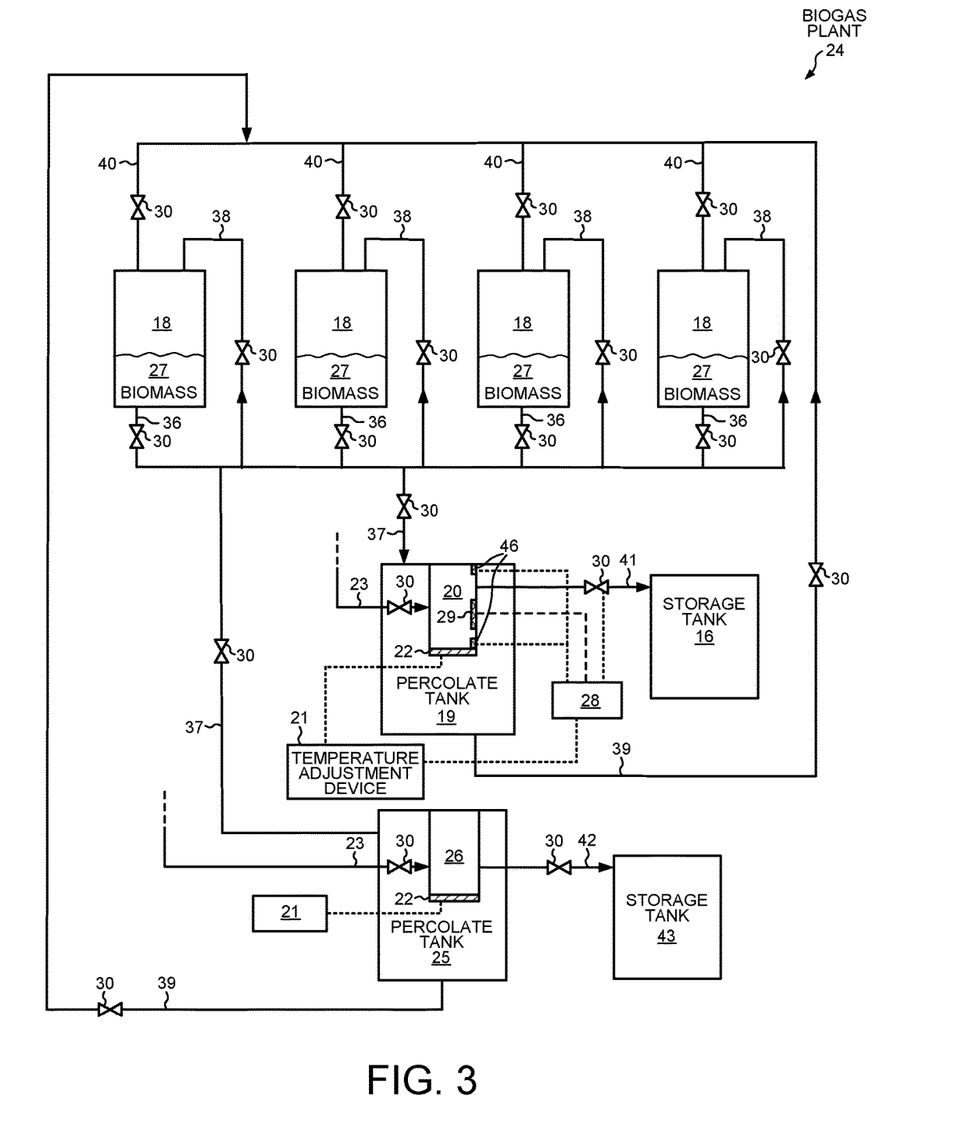
FIG. 3 is a biogas plant according to a third embodiment of the invention.

The biogas plant 24 of FIG. 3 includes several fermenters 18 and/or several percolate tanks 19, 25 and/or several sanitation tanks 20, 26. Each of the several percolate tanks 19, 25 is connected with at least one of the several fermenters 18 in a percolate circuit. Each of the several sanitation tanks is connected with at least one of the several percolate tanks 20, 26 for the intake of percolate 13. Each of the sanitation tanks 20, 26 includes a temperature adjustment device 21 for maintaining the temperature of the percolate within a temperature range of $65°>T>45°$, preferably $60°>T>50°$, so as to support a thermophilic fermentation sanitation treatment of the percolate. The use of several fermenters 18 and/or several percolate tanks 19 and/or several sanitation tanks 20 not only increases the productivity of the fermentation and sanitation process, but also makes the biogas plant more flexible. This is advantageous in particular when the biomass 27 to be fermented is heterogeneous in its composition in order to produce biogas in an efficient and effective manner. In particular, it is advantageous to use different bacterial cultures for different biomass substrates. Preferably, each fermenter 18 is connected to each percolate tank 19, 25 and each sanitation tank 20, 26 to form a network of fermenters and tanks that cooperate with each other. Furthermore, the operation of the biogas plant 24 can be continued mostly unimpeded in case of maintenance work or in case of a malfunction incident. Alternatively there are several sanitation tanks 20 in one single percolate tank 19, or several sanitation and percolate tanks can be connected with each other in a cascade. Although the biogas plant 24 can include any number of fermenters 18 and sanitation and percolate tanks, a complex biogas plant preferably includes sub-units each with one fermenter 18, one sanitation tank 20, and one percolate tank 19. The sanitation tank 20 and percolate tank 19 that produce biogas from the biomass 27 based on the principle of dry fermentation can be part of a biogas plant for the production of biogas from biomass based on the principle of wet fermentation.

The biogas plant 24 includes a control system 28 for controlling all its components. This is expedient in particular for maintaining the temperature of the percolate within a range that promoted a thermophilic treatment of the percolate. The components controlled by the control system 28 include temperature sensors 29, the temperature adjustment devices 21, valves 30, fill level sensors 46, leak detectors, devices for the registration of malfunctions in electrical installations, etc.

FIG. 1 shows a schematic illustration of principles used by a first embodiment of the biogas plant 10. Percolate 13 is circulated between the solid fermenter 14 containing biomass 27 and the percolate tank 11 using a first percolate pipe 31 and a second percolate pipe 32. Excess percolate is discharged into the sanitation tank 12 via a third percolate pipe 33. When the percolate 13 in the sanitation tank 12 has reached a sufficient fill level, the connection between the percolate tank 11 and the sanitation tank 12 is disconnected, and the percolate is sanitized in the sanitation tank 12 by thermophilic processes. Upon completion of sanitation, liquid fertilizer in the form of the sanitized percolate 15 is drained from the sanitation tank 12 via a fourth percolate pipe 34. Via a fifth percolate pipe 35, contaminated percolate 13 can also be discharged directly from the fermenter 14 into the sanitation tank 12. During sanitation, the percolate pipe 35 is disconnected. The disconnection of the sanitation tank 12 from the percolate circuit with percolate tank 11 and fermenter 14 is performed by valves 30. This safely prevents contaminated percolate 13 from entering the sanitation tank 12 during sanitation. Because percolate tank 11 and sanitation tank 12 are different components, biogas production in the fermenter 14 and sanitation in the sanitation tank 12 can be carried out in parallel.

FIG. 2 shows a second embodiment of a biogas plant 17 with several fermenters 18. In accordance with the operating processes illustrated in FIG. 1, the biogas plant 17 has a percolate tank 19 into which contaminated percolate 13 is emptied. The biogas plant 17 includes four fermenters 18 that are connected to the percolate tank 19 by percolate pipes 36 that all empty into a first main percolate pipe 37. Percolate return pipes 38 run from the first main percolate pipe 37 back to the respective fermenters 18 in order to sprinkle the biomass 27 (the substrate) contained in the fermenters 18 with percolate 13 enriched with bacteria and to moisten the biomass during the dry fermentation process. Percolate 13 from the percolate tank 19 can also be sprinkled over the biomass 27. A second main percolate pipe 39 supplies percolate 13 from the percolate tank 19 to the respective fermenters 18 via secondary percolate pipes 40.

In addition, the biogas plant 17 includes a sanitation tank 20 located inside the percolate tank 19 in an elevated position coaxially to the percolate tank 19 in such a way that its upper end is on the same level as the top end of the percolate tank 19, as it is shown in FIG. 2. The biogas plant 17 also includes a storage tank 16 connected to the sanitation tank 20 via a percolate discharge pipe 41. For this reason, the side panels and the bottom of the sanitation tank 20 are completely in contact with percolate when the percolate tank 19 is completely filled with percolate.

The percolate 13 is caused to flow through the pipes 36-41 using pumps (not shown) and stop valves 30 that are each controlled by a control unit 28. The direction of the flow of percolate 13 is shown in FIG. 2 with arrows on the pipes 36-41. The percolate pipe 23 represents a pipe that supplies contaminated percolate 13 from the fermenters 18 to the sanitation tank 20 for thermophilic sanitation (decontamination).

The second embodiment of biogas plant 17 shown in FIG. 2 includes four individual percolate circuits that operate using four separate percolate return pipes 38. Biogas plant 17 also has a main percolate circuit that operates using the second main percolate pipe 39. The percolate circuits can be switched separately from each other and in any combination. The percolate 13 can be supplied only to individual fermenters 18 or to all fermenters via the second main percolate pipe 39 by opening or closing the appropriate valves 30 in the secondary percolate pipes 40.

FIG. 3 shows a biogas plant 24 according to a third embodiment that differs from the second embodiment in that it includes a second percolate tank 25 and an additional storage tank 43. Second percolate tank 25 includes a sanitation tank 26. Second percolate tank 25 is similarly connected to each of the fermenters 18 by percolate pipe 37, and the additional sanitation tank 26 is connected to the additional storage tank 43 by an additional percolate discharge pipe 42.

This means that the biogas plant 24 of the third embodiment is derived from the biogas plant 17 of the second embodiment by adding an additional one of the tank units 44 that is outlined by the dashed line in FIG. 2. The additional tank unit 44 with percolate tank 25 and storage tank 43 is connected in a functionally equivalent way to the first tank unit with percolate tank 19 and storage tank 16. Consequently, the biogas plant 24 of the third embodiment includes an additional percolate circuit that returns percolate 13 from the additional percolate tank 25 to the fermenters 18.

Figure 4:
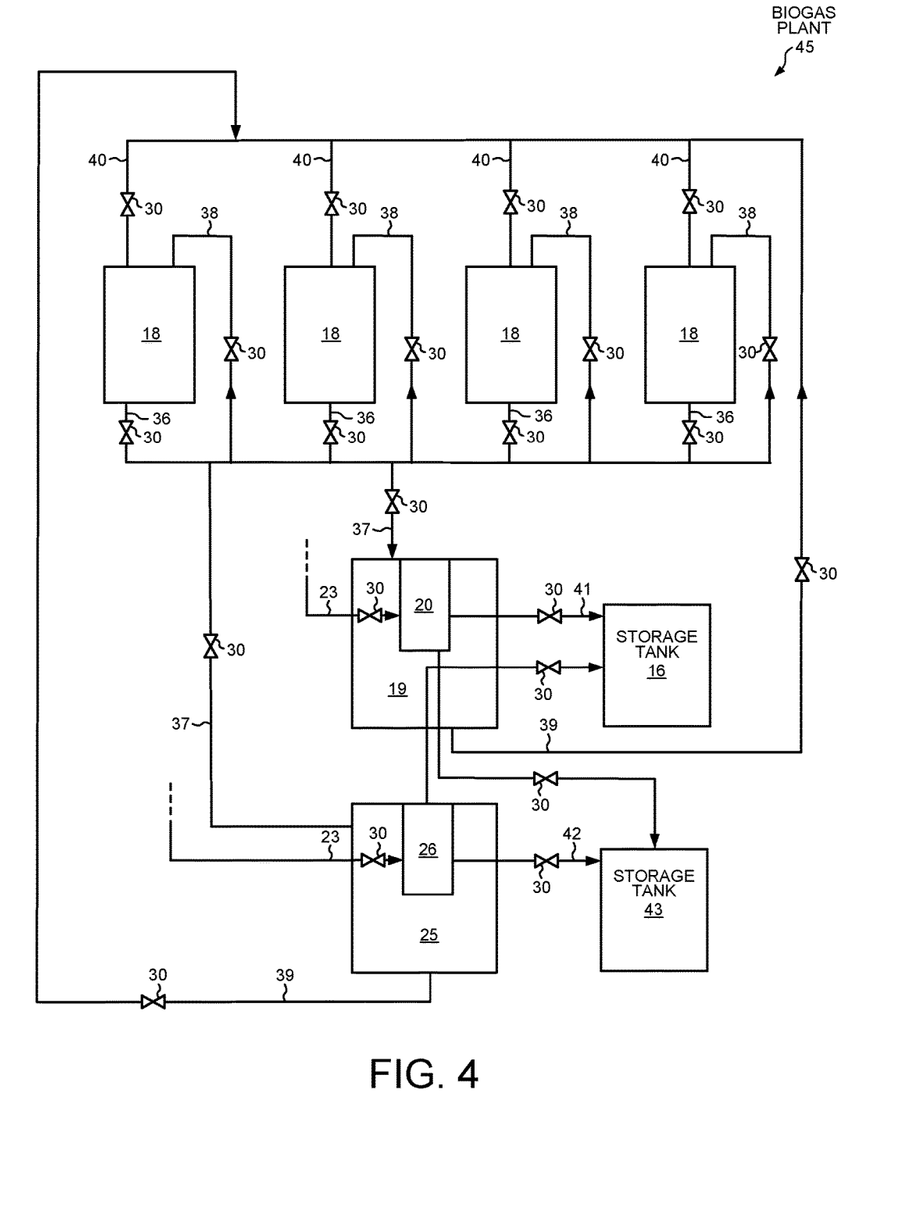
FIG. 4 is a biogas plant according to a fourth embodiment of the invention.

FIG. 4 shows a biogas plant 45 according to a fourth embodiment that differs from the biogas plant 24 of the third embodiment in that the two sanitation tanks 20 and 26 are additionally cross connected with the two storage tanks 16 and 43.

Although the present invention has been described in connection with certain specific embodiments for instructional purposes, the present invention is not limited thereto. Accordingly, various modifications, adaptations, and combinations of various features of the described embodiments can be practiced without departing from the scope of the invention as set forth in the claims.

What is claimed is:

1. A method for producing liquid fertilizer, comprising:
    fermenting biomass in a fermenter using dry fermentation, wherein the fermenting generates percolate;
    circulating the percolate between the fermenter and a percolate tank;
    transferring a first portion of the percolate from the percolate tank into a sanitation tank;
    sanitizing the percolate contained in the sanitation tank using a thermophilic fermentation reaction at a Celsius temperature between 45° and 65° for a period of at least five days; and
    draining the sanitized percolate as the liquid fertilizer from the sanitation tank.

2. The method of claim 1, further comprising:
    transferring a second portion of the percolate from the percolate tank into the sanitation tank after the draining of the sanitized percolate from the sanitation tank.

3. The method of claim 1, wherein the first portion of the percolate is transferred from the percolate tank into the sanitation tank when a fill level sensor indicates that the sanitation tank is empty.

4. The method of claim 1, wherein the first portion of the percolate is transferred from the percolate tank into the sanitation tank when a fill level sensor indicates that the percolate tank is full.

5. The method of claim 1, wherein the sanitized percolate is drained from the sanitation tank into a storage tank.

6. The method of claim 5, wherein the first portion of the percolate is transferred from the percolate tank into the sanitation tank when a fill level sensor indicates that the storage tank has been drained.

7. The method of claim 1, wherein the first portion of the percolate passes through a valve from the percolate tank into the sanitation tank, and wherein the valve is closed during the sanitizing.

8. A method comprising:
    generating methane by fermenting biomass in a fermenter, wherein the fermenting generates a percolate;
    transferring the percolate from the fermenter to a percolate tank;
    returning the percolate from the percolate tank to the fermenter and sprinkling the percolate over the biomass;

transferring a first portion of the percolate from the percolate tank into a sanitation tank;

heating the percolate contained in the sanitation tank to a Celsius temperature between 45° and 65° for a period of at least five days; and draining the percolate from the sanitation tank.

9. The method of claim 8, wherein the sanitation tank is arranged concentrically inside the percolate tank.

10. The method of claim 9, wherein the heating of the percolate contained in the sanitation tank is performed using heat generated from a thermophilic fermentation reaction occurring in the percolate tank.

11. The method of claim 8, further comprising:

transferring a second portion of the percolate from the percolate tank into the sanitation tank after the draining the percolate from the sanitation tank.

12. The method of claim 8, wherein the first portion of the percolate is transferred from the percolate tank into the sanitation tank when a fill level sensor indicates that the sanitation tank is empty.

13. The method of claim 8, wherein the first portion of the percolate passes through a valve from the percolate tank into the sanitation tank, and wherein the valve is closed during the period of at least five days when the percolate contained in the sanitation tank is heated to the Celsius temperature between 45° and 65°.

* * * * *